United States Patent
Szewczyk et al.

(10) Patent No.: US 10,130,370 B2
(45) Date of Patent: Nov. 20, 2018

(54) MEDICAL RESTRICTION DEVICE FOR HOLLOW ORGANS OF A BODY

(75) Inventors: Tomasz Szewczyk, Lodz (PL); Frank Claessen, Maaseik (BE)

(73) Assignee: Q MEDICAL INTERNATIONAL AG, Stein am Rhein (CH)

( * ) Notice: Subject to any disclaimer, the term of this patent is extended or adjusted under 35 U.S.C. 154(b) by 736 days.

(21) Appl. No.: 13/996,411

(22) PCT Filed: Dec. 14, 2011

(86) PCT No.: PCT/EP2011/072801
§ 371 (c)(1),
(2), (4) Date: Jun. 20, 2013

(87) PCT Pub. No.: WO2012/084653
PCT Pub. Date: Jun. 28, 2012

(65) Prior Publication Data
US 2013/0296900 A1 Nov. 7, 2013

(30) Foreign Application Priority Data
Dec. 23, 2010 (EP) .................... 10196846

(51) Int. Cl.
*A61B 17/12* (2006.01)
*A61F 5/00* (2006.01)

(52) U.S. Cl.
CPC ...... *A61B 17/12022* (2013.01); *A61F 5/0063* (2013.01); *A61F 5/0066* (2013.01)

(58) Field of Classification Search
CPC ........ A61B 17/12022; A61B 17/00234; A61B 19/54; A61B 17/12009; A61F 5/0066; A61F 5/0063; A61F 5/005
See application file for complete search history.

(56) References Cited

U.S. PATENT DOCUMENTS 5,601,604 A * 2/1997 Vincent .................. A61F 5/003
606/216
6,676,674 B1 * 1/2004 Dudai .................... A61B 17/12
606/151
(Continued)

FOREIGN PATENT DOCUMENTS

EP 1778098 A2 5/2007
EP 1829505 A2 9/2007
(Continued)

OTHER PUBLICATIONS

International Search Report dated Mar. 6, 2012, as issued in corresponding International Patent Application No. PCT/EP2011/072801, filed Dec. 14, 2011 (with English translation—7 pages).

*Primary Examiner* — Jocelin Tanner
(74) *Attorney, Agent, or Firm* — Maier & Maier, PLLC

(57) ABSTRACT

The invention relates to a medical restriction device for hollow organs of a body, having a longitudinal flexible element having a first and a second end, a closure device locking the longitudinal element annularly in a predetermined diameter position, and a tip as an insertion aid at the first end of the longitudinal element for placing the restriction device on the hollow organ, wherein the tip comprises a reinforcing core made of rigid material, wherein an opening is provided at the second end of the longitudinal element as part of the closure device, the tip can be inserted with the first end of the longitudinal element into the opening at the second end of the longitudinal element for locking the closure device, and the tip is fixedly connected to the first end; and can be cut off after locking the longitudinal element by the closure device.

14 Claims, 2 Drawing Sheets

(56) References Cited

U.S. PATENT DOCUMENTS

| | | | |
|---|---|---|---|
| 7,618,365 B2 * | 11/2009 | Jambor | A61F 5/0066 600/37 |
| 7,828,813 B2 * | 11/2010 | Mouton | A61F 5/005 600/37 |
| 2007/0185374 A1 * | 8/2007 | Kick | A61B 17/00234 600/37 |
| 2008/0287975 A1 * | 11/2008 | Weaner | A61F 5/0056 606/157 |
| 2009/0306463 A1 | 12/2009 | Mouton et al. | |
| 2010/0152705 A1 * | 6/2010 | Navis | A61M 25/0041 604/523 |
| 2012/0022320 A1 * | 1/2012 | Hendrickx | A61F 5/005 600/37 |

FOREIGN PATENT DOCUMENTS

| | | | |
|---|---|---|---|
| FR | 2941366 | * | 1/2009 |
| WO | 02096326 A2 | | 12/2002 |
| WO | 2005117716 A2 | | 12/2005 |

* cited by examiner

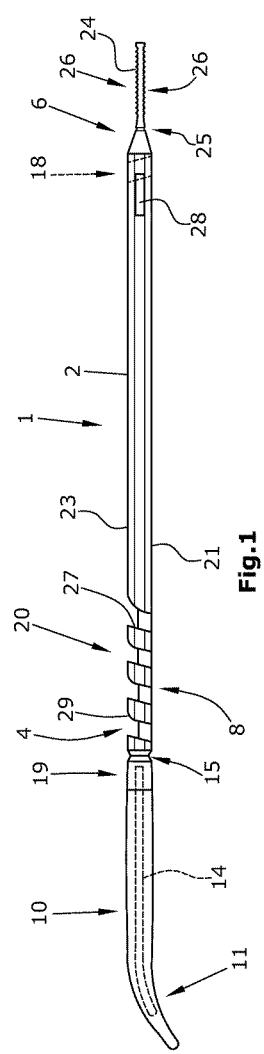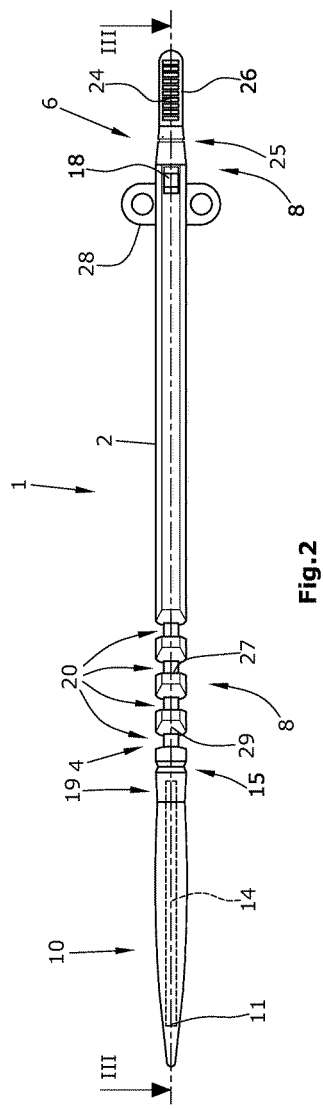

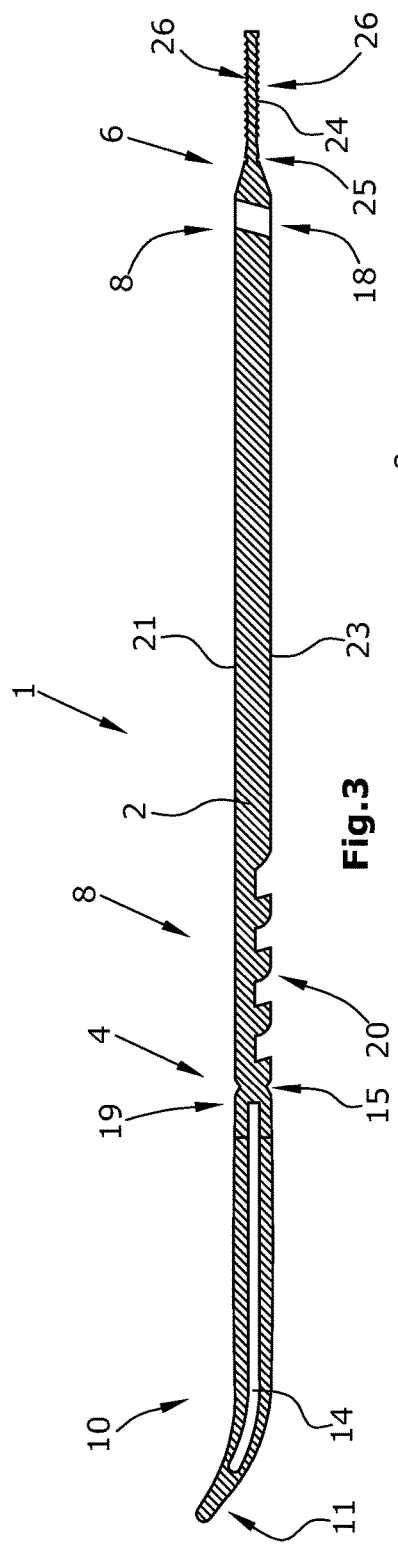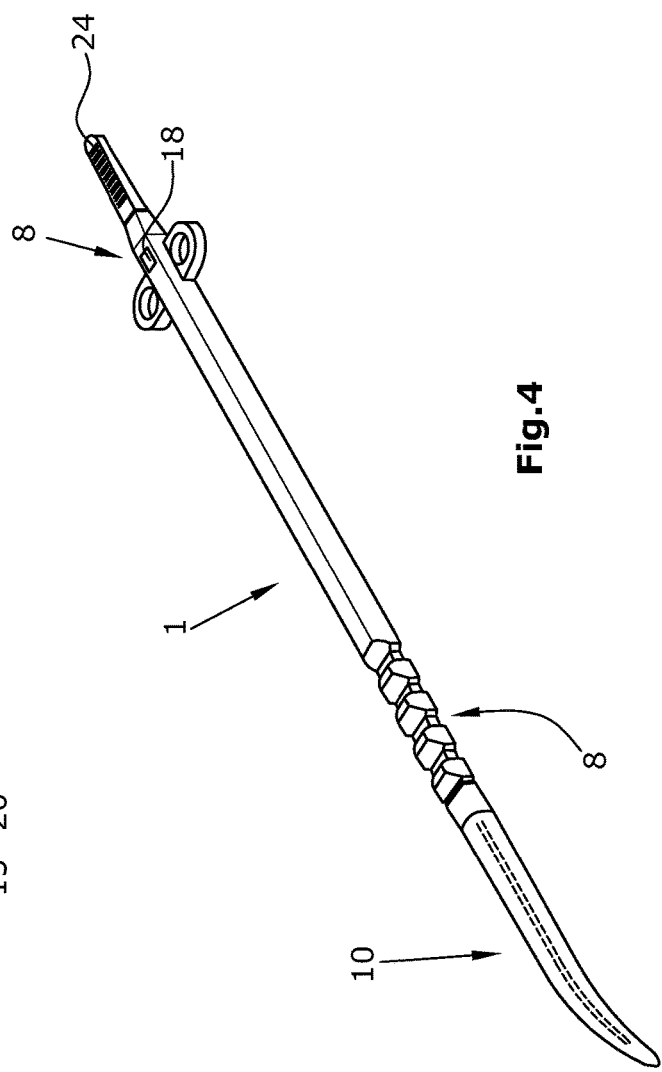

MEDICAL RESTRICTION DEVICE FOR HOLLOW ORGANS OF A BODY

RELATED APPLICATIONS

This is the U.S. national stage application which claims priority under 35 U.S.C. § 371 to International Patent Application No.: PCT/EP2011/072801 filed on Dec. 14, 2011, which claims priority to European Patent Application No. 10196846.9 filed on Dec. 23, 2010, the disclosures of which are incorporated by to reference herein their entireties.

The present invention relates to a medical restriction device for hollow organs of a body according to the preamble of claim 1.

Such medical restriction devices for hollow organs are described in EP 1 778 098 A, for example. The known restriction device comprises a longitudinal flexible element with a first and a second end, which, however, is not extensible in the longitudinal direction.

A closure device locks the longitudinal element annularly in a single predetermined diameter position. For different diameters, different restriction devices must be kept in store. A pull-off tip at the first end serves as an inlet guide of the longitudinal element for positioning the restriction device at the hollow organ.

Starting from such prior art, it is an object of the present invention to provide an improved restriction device that is easier to manipulate during the application thereof.

In order to achieve this object, the invention provides that
the tip comprises a reinforcing core of rigid material,
an opening is provided at the second end of the longitudinal element as a part of the closure device,
the tip is adapted to be inserted together with the first end of the longitudinal element into the opening at the second end of the longitudinal element in order to lock the closure device, and
the tip is firmly connected with the first end and can be severed after the longitudinal element has been locked by the closure device.

The invention has the following advantages: due to the tip provided with a reinforcing core, the restriction device can be passed better around the hollow organ and can more easily penetrate the elastic and fibrous connective tissue surrounding a hollow organ and holding the same in position. In combination with the opening at the second end of the longitudinal element, the tip can be passed more easily through the opening in order to lock the restriction device in a predetermined or selectable position when the closure device is in the closed position. Advantageously, the tip is first integrally connected with the first end and can be severed after the longitudinal element is locked by the closure device so that the tip does not have to remain at the hollow organ and the restriction device can surround the hollow organ annularly. The tip may preferably be cut off at a notch, for example, with a pair of scissors after the restriction device is locked in its closed position by the closure device.

Preferably, it is provided that the longitudinal element is made of a material that is extensible to a low degree. The maximum allowable extension is between about 1% and about 20%, preferably between about 1% and 10%.

In an advantageous development it is provided that the closure device is adapted to lock the longitudinal element in a plurality of selectable diameter positions. For example, the restriction device can be locked in four diameter positions.

For this purpose, the longitudinal element comprises the opening at the second end, which is adapted to cooperate with one of a plurality, e.g. four, notches at the first end in order to lock the restriction device in one of a plurality of latching positions.

To achieve this, the notches and the opening are matched such that the closure device formed thereby enables a locking in the respective positions. Thereby, the restriction device is more versatile, i.e. it can be used for different diameters, and it can be adapted to the diameter of the hollow organ.

Preferably, it is provided that the closure device at the first end of the longitudinal element comprises notches matched to the opening at the second end of the longitudinal element, and that the opening at the second end cooperates elastically with the notches and engages the notches in order to lock the longitudinal element annularly in one of a plurality of selectable diameter openings.

The notches are elastic and also enable a posterior widening of the restriction device prior to severing the tip, e.g. by locking the closure device in the next successive notch seen in the direction of the tip.

Due to the flexible material, it is possible to change the latching position even after the closing of the closure device and to choose another latching position determined by the notches in the longitudinal element.

The restriction device is adapted for laparoscopic use and for insertion into the body via the opening of a trocar. For this purpose, the dimensions of the restriction device are adapted to the rated diameter of a trocar, e.g. an opening of 10 mm, so that the restriction device can be inserted through the trocar in the open state of the device.

In another development of the invention, it is provided that the second end comprises a pull tab severable after the restriction device is closed.

The pull tab can be held with a suitable gripping instrument and provides sufficient counter-support when the tip of the longitudinal element is inserted into the opening at the second end and is eventually pulled through the opening.

After the restriction device has been locked, the pull tab can also be severed from the restriction device. For this purpose, a rated cut-off point may be provided on the end of the pull tab directed to longitudinal element.

At least two fixation eyelets may be provided at the second end. These fixation eyelets arranged near the opening at the second end make it possible to sew the restriction device to the hollow organ after the restriction device has been positioned exactly.

The pull tab may have a friction-increasing surface at the second end so that the gripping instrument has a better hold on the pull tab.

The restriction device is radio-opaque (impermeable to radiation). Preferably, the entire restriction device is radio-opaque. This is of importance, if the severable tip gets lost, since it can thus be located in the body.

In a preferred embodiment it is provided that the reinforcing core or the tip of the reinforcing core is pre-curved towards the curvature of the restriction device which is annular in the closed position, and that the reinforcing core includes metal or hard plastics. The rigid reinforcing core can also be made of metal or hard plastics and, for the rest, is surrounded by the silicon material of the restriction device. The curvature of the tip, in combination with its rigidity caused by the reinforcing core, facilitates the insertion of the tip into the opening at the second end of the longitudinal element and facilitates locking the closure device In a preferred embodiment it is provided that the notches and the opening of the closure device at the second end of the longitudinal element are matched in a form fitting manner, e.g. conically or tapered. In this manner, the restriction device is securely retained in the different diameter positions by the closure device, while, by applying greater force, the engagement positions can nevertheless be overcome to widen the diameter of the restriction device. Thus, the latching position once assumed is also reversible, if a diameter position that is too tight has erroneously been set at first.

The restriction device is made preferably of a transparent or colored material. The material of choice is a medical silicone, e.g. unrestricted NuSil silicone.

At least in the region of the longitudinal element, the restriction device may have a predetermined curvature caused by tempering at a predetermined temperature.

The following is a detailed description of embodiments of the invention with reference to the drawing.

In the Figures:

FIG. 1 is a side elevational view of a first embodiment of a medical restriction device, FIG. 2 is a top plan view on the embodiment in FIG. 1, FIG. 3 is a section along the line A-A in FIG. 2, and FIG. 4 is a perspective view.

The medical restriction device 1 for hollow organs of a body, illustrated in FIGS. 1 to 4, comprises a longitudinal flexible element 2 with a first end 4 and a second end 6. At the first end 4, a severable tip 10 is firmly connected with the longitudinal element 2. For example, the longitudinal element has a width of about 4.5 mm and a height of about 3 mm, seen in cross section.

A closure device 8 enables to lock the first end 4 to the second end 6 in a predetermined selectable diameter position, the longitudinal element 2 extending annularly around a hollow organ.

The tip 10 can be severed at a predefined cut-off position 15 after the longitudinal element 2 has been locked by the closure device 8. At the end directed to the longitudinal element 2, the tip 10 may be provided with ribbings for a gripping instrument, which have a friction-increasing effect when the restriction device 1 is handled with a griping instrument, so that the gripping instrument cannot slip off. If the restriction device 1 is not manufactured in one piece, a coupling element 19 may be provided in the direction of the tip 10 near the cut-off position 15, by means of which element the tip 10 can be connected posteriorly, e.g. by gluing the same to the first end 4 of the longitudinal element 2.

The tip 10 comprises a reinforcing core 14 of a rigid material, e.g., metal or hard plastics.

The reinforcing core 14 may at first extend linearly or, in the direction of the free end 11 of the tip, it may be curved slightly towards the inner surface 21 of the restriction device 1. The reinforcing element 14 is surrounded by the material of the restriction device 1 which is made preferably of medical silicone (NuSil). The silicone material tapers at the distal end of the tip 10 and extends beyond the reinforcing element 14 so that the free end 11 of the tip 10 can be moved in a flexible manner.

A illustrated in the top plan view in FIG. 2, the closure element 8 is formed by a preferably rectangular opening 18 arranged obliquely in the longitudinal element 2 at the second end 6, as well as by a plurality of notches 20 in the material of the longitudinal element 2. For example, the opening 18 extends under an angle of 15° with respect to the inner surface 21 of the longitudinal element 2. In this embodiment, the notches 20 define four latching positions, with the opening 18 engaging in one of the notches 20. For this purpose, the tip 10 is pulled through the opening 18 until the desired latching position is reached. Due to the four notches 20, it is possible to set four different diameters of the restriction device 1. Here, the restriction device 1 surrounds the hollow organ annularly. The notches 20 are formed by recesses in the longitudinal element 2. In the embodiment shown in FIGS. 1 to 4, the recesses are provided in the outer surface 23 of the longitudinal element 2, whereas the inner surface 21 of the longitudinal element 2 continuously lies on one plane. In addition, as can be seen in top plan view in FIG. 1, the notches 20 can be formed by lateral recesses in the material. The shape of the notches 20 is matched to the shape of the opening 18, so that the opening 18 can engage and enclose the notches 20 in a form-fitting manner.

As can be seen in FIG. 2, the side walls 27 of the notch 20 extend under an angle that is equal to the angle of the inclines opening, e.g., 15°.

The mutual distance between the notches 20 may be 5 mm, for instance. The length of the element 2 between the opening and the outer notch 20 is, for instance, between 80 mm and 90 mm, preferably 83 mm. The overall length of the restriction device 1 is, for instance, 150 mm to 160 mm, preferably 154 mm.

At the first end 6, the longitudinal element 2 is formed with a pull tab 24 which has a flattened shape and may have ribbings 26 on the upper and lower surfaces in order to increase the friction of a gripping instrument. The pull tab 24 is formed integrally with the longitudinal element 2, but it can be severed at a rated cut-off position after the restriction device 1 has been closed.

Near the opening 18, a fixation eyelet 18 may be arranged by which the restriction device 1 can be attached to the hollow organ, e.g. by sewing, after it has been positioned around the same. On the side facing the first end 4, the notches 20 are rounded at their flanks so that the second end with the opening 18 can be pulled more easily into the tighter locking positions. In contrast thereto, the flanks facing the first end 4 are linear in order to guarantee a secure locking position. Still, due to the flexibility of the material, it is possible, if so desired, to leave a tighter engagement position by exerting greater force in order to set a locking position with a larger diameter of the restriction device 1.

The restriction device 1 of all embodiments has a diameter, seen in cross section, which allows inserting the restriction device 1 in the open state through the opening of a trocar into the body. Since the fixation eyelets 28 are made from a flexible silicone material, the fixation eyelets 28 can flex and thus do not hinder the insertion of the restriction device 1 into a trocar.

The restriction device 1 is radio-opaque. This means that it is impermeable to radiation and is thus visible in an x-ray examination, for instance.

The silicone material of the restriction device 1 may be transparent or colored. For example, the restriction device 1 could be colored in blue for a better distinction from tissue when observed with the human eye or on a monitor via a camera.

The restriction device 1 may be given a predetermined curvature at least in the region of the longitudinal element, which is caused by tempering at a predetermined temperature.

The invention claimed is:

1. A medical restriction device for a hollow organ of a body, comprising:

a longitudinal flexible element having a first and a second end, a closure device for locking the longitudinal element annularly in a predetermined diameter position, and a tip as an inlet guide at the first end of the longitudinal element for positioning the restriction device at the hollow organ, wherein the tip comprises a reinforcing core of rigid material surrounded by a silicone material, an opening is provided in the second end of the longitudinal element as a part of the closure device, the tip is adapted to be inserted together with the first end of the longitudinal element into the opening at the second end of the longitudinal element in order to lock the closure device, the tip is firmly connected with the first end and can be severed after the longitudinal element has been locked by the closure device, the reinforcing core of the tip is curved, a curvature of the tip, in combination with its rigidity caused by the reinforcing core, facilitates the insertion of the tip into the opening of the second end of the longitudinal element and facilitates locking the closure device, and the longitudinal element is made of a material that is extensible, wherein a maximum extension is between 1% and 20%.

2. The medical restriction device of claim 1, wherein the closure device is adapted to reversibly lock the longitudinal element in a plurality of diameter positions.

3. A medical restriction device for a hollow organ a body, comprising:

a longitudinal flexible element having a first and a second end, a closure device for locking the longitudinal element annularly in a predetermined diameter position, and a tip as an inlet guide at the first end of the longitudinal element for positioning the restriction device at the hollow organ, the tip comprising a reinforcing core of rigid material surrounded by a silicone material, wherein an opening is provided in the second end of the longitudinal element as a part of the closure device, the tip is adapted to be inserted together with the first end of the longitudinal element into the opening at the second end of the longitudinal element in order to lock the closure device, the tip is firmly connected with the first end and can be severed after the longitudinal element has been locked by the closure device, and the closure device is adapted to reversibly lock the longitudinal element in a plurality of diameter positions, wherein the closure device comprises the opening at the second end, which cooperates with one of a plurality of notches at the first end, wherein the notches are elastic and enable a posterior widening of the medical restriction device prior to severing the tip, wherein the longitudinal element is made of a material that is extensible, wherein a maximum extension is between 1% and 20%.

4. The medical restriction device of claim 3, wherein the longitudinal element is made of a solid material that is extensible to a low degree.

5. The medical restriction device of claim 3, wherein the restriction device is adapted for laparoscopic use and is adapted for insertion into the body via the opening of a trocar.

6. The medical restriction device of claim 5, wherein the closure device at the first end of the longitudinal element has notches adapted to the opening at the second end of the longitudinal element, in that the opening at the second end elastically cooperates with the notches and engages the notches in order to lock the longitudinal element annularly in one of a plurality of selectable diameter positions.

7. The medical restriction device of claim 6, wherein the notches and the opening of the closure device are matched in a form fitting manner.

8. The medical restriction device of claim 3, wherein the second end comprises a pull tab adapted to be severed after the restriction device is closed.

9. The medical restriction device of claim 3, wherein at least two fixation eyelets are provided at the second end.

10. The medical restriction device of claim 8, wherein the pull tab at the second end has a surface that increases friction.

11. The medical restriction device of claim 3, wherein the restriction device is radio-opaque.

12. The medical restriction device of claim 3, wherein the tip comprises a reinforcing core of rigid material, that the reinforcing core or the tip of the reinforcing core is pre-curved towards the curvature of the restriction device which is annular in a closed position, and that the reinforcing core includes metal or hard plastics.

13. The medical restriction device of claim 3, wherein the restriction device is made from a transparent or colored material.

14. The medical restriction device of claim 3, wherein at least the longitudinal element of the restriction device has a predetermined curvature caused by tempering at a predetermined temperature.

* * * * *